US00PP19240P2

(12) United States Plant Patent
Gilford et al.

(10) Patent No.: US PP19,240 P2
(45) Date of Patent: Sep. 16, 2008

(54) STRAWBERRY PLANT NAMED 'DRISSTRAWFOUR'

(50) Latin Name: *Fragaria×ananassa*
Varietal Denomination: DrisStrawFour

(75) Inventors: Kristie L. Gilford, Dover, FL (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 11/974,124

(22) Filed: Oct. 11, 2007

(51) Int. Cl.
*A01H 5/00* (2006.01)

(52) U.S. Cl. ..... Plt./208

(58) Field of Classification Search ..... Plt./208
See application file for complete search history.

*Primary Examiner*—Annette H Para
(74) *Attorney, Agent, or Firm*—Jondle & Associates, P.C.

(57) ABSTRACT

This invention relates to a new and distinct cultivar of strawberry plant named 'DrisStrawFour'. A new cultivar primarily characterized by its large fruit size, heavy fruit production, moderate resistance to *Lygus hesperus, Botrytis* fruit rot, powdery mildew, and Strawberry Mottle Virus and resistance to *Verticillium* wilt is disclosed.

3 Drawing Sheets

Genus and species: *Fragaria×ananassa.*
Variety denomination: 'DrisStrawFour'.

BACKGROUND OF THE NEW PLANT

The present invention relates to a new and distinct strawberry cultivar designated 'DrisStrawFour' and botanically known as *Fragaria×ananassa.* This new strawberry cultivar was discovered in December, 2000 and originated from a cross between the female parent '6F364', a proprietary strawberry plant (unpatented) and the male parent 'Mirador' (U.S. Plant Pat. No. 11,279). The original seedling of the new cultivar was asexually propagated at a nursery in Shasta County, California. 'DrisStrawFour' was subsequently asexually propagated and underwent further testing at a nursery in Hillsborough County, Florida for six years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
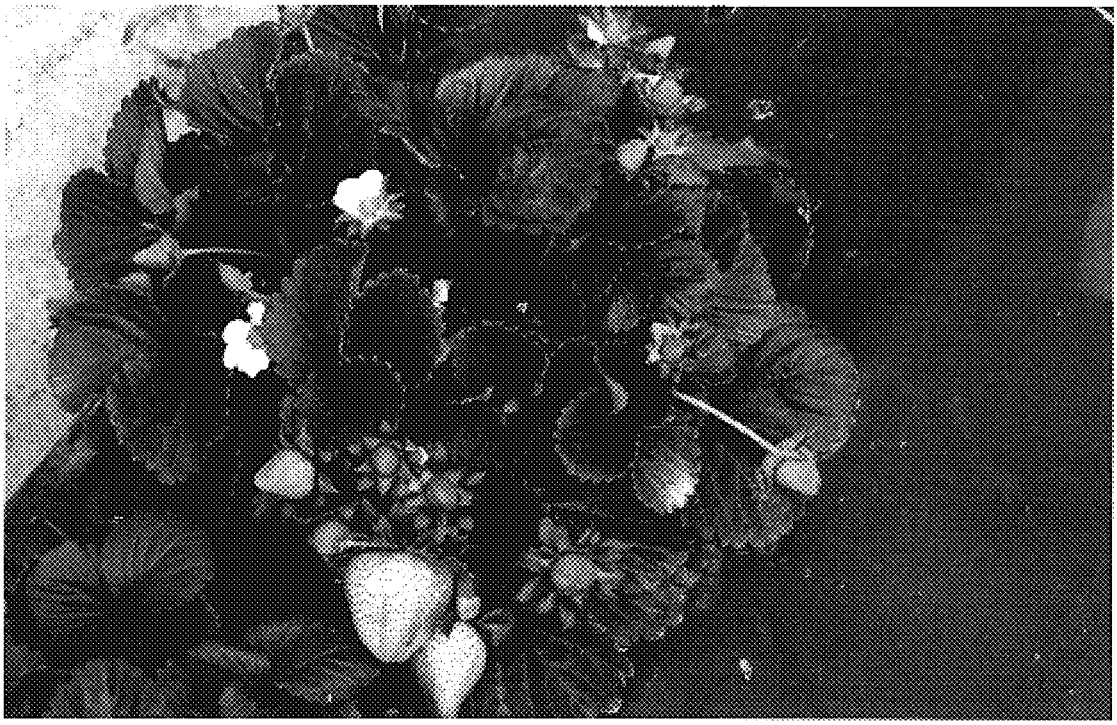
FIG. 1 shows overall plant habit including fruit at various stages of development.
Figure 2:
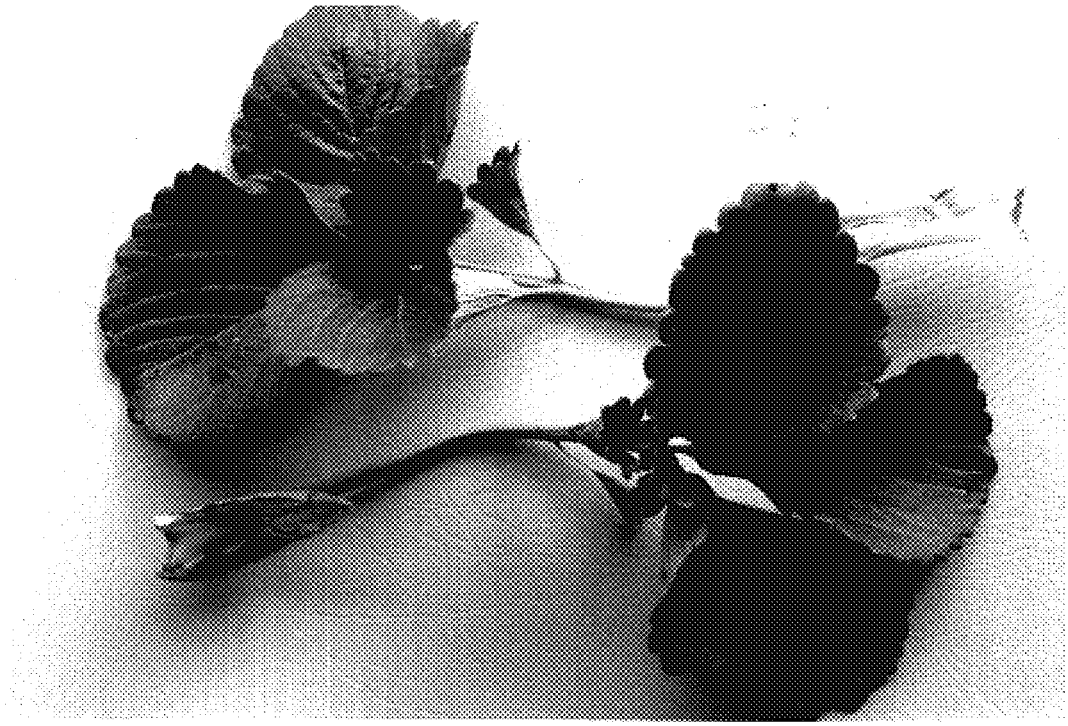
FIG. 2 shows leaves of the plant with three leaflets.
Figure 3:
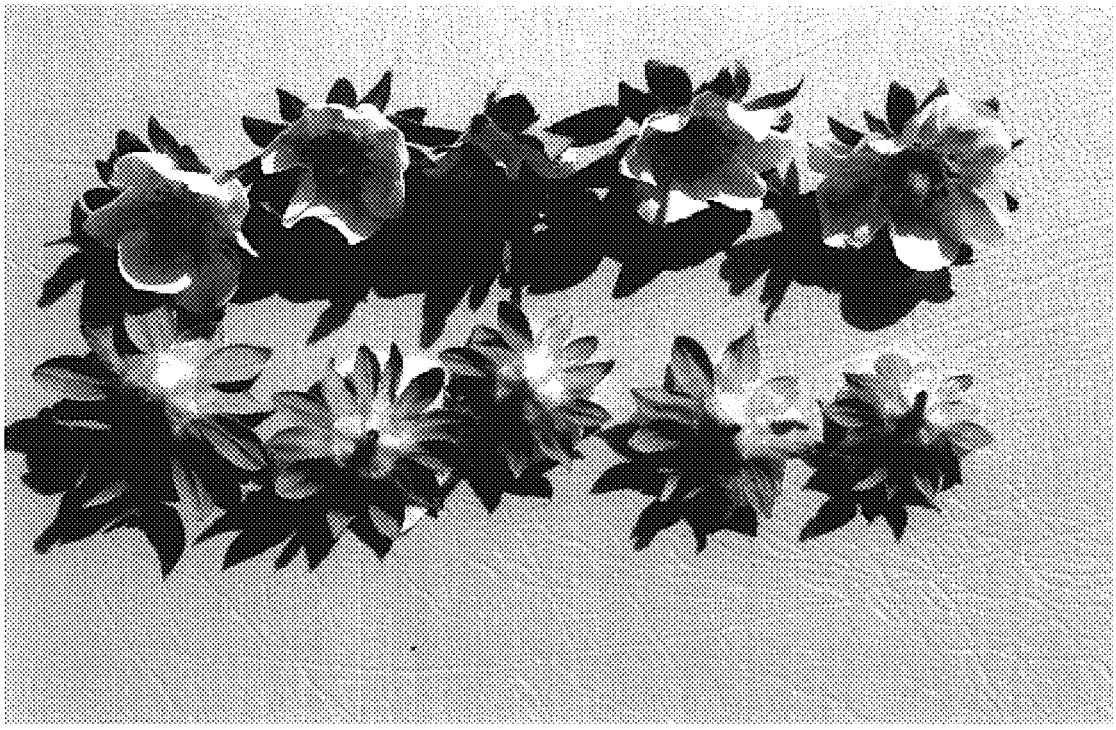
FIG. 3 shows both the upperside and underside of several of the flowers.
Figure 4:
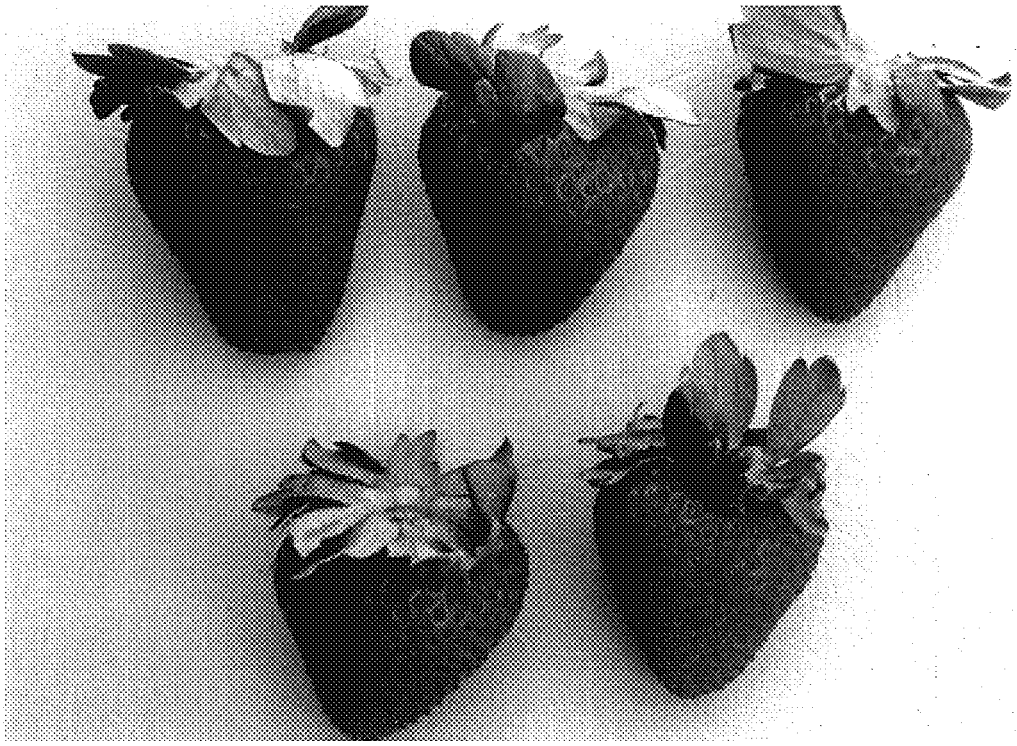
FIG. 4 shows the whole fruit.
Figure 5:
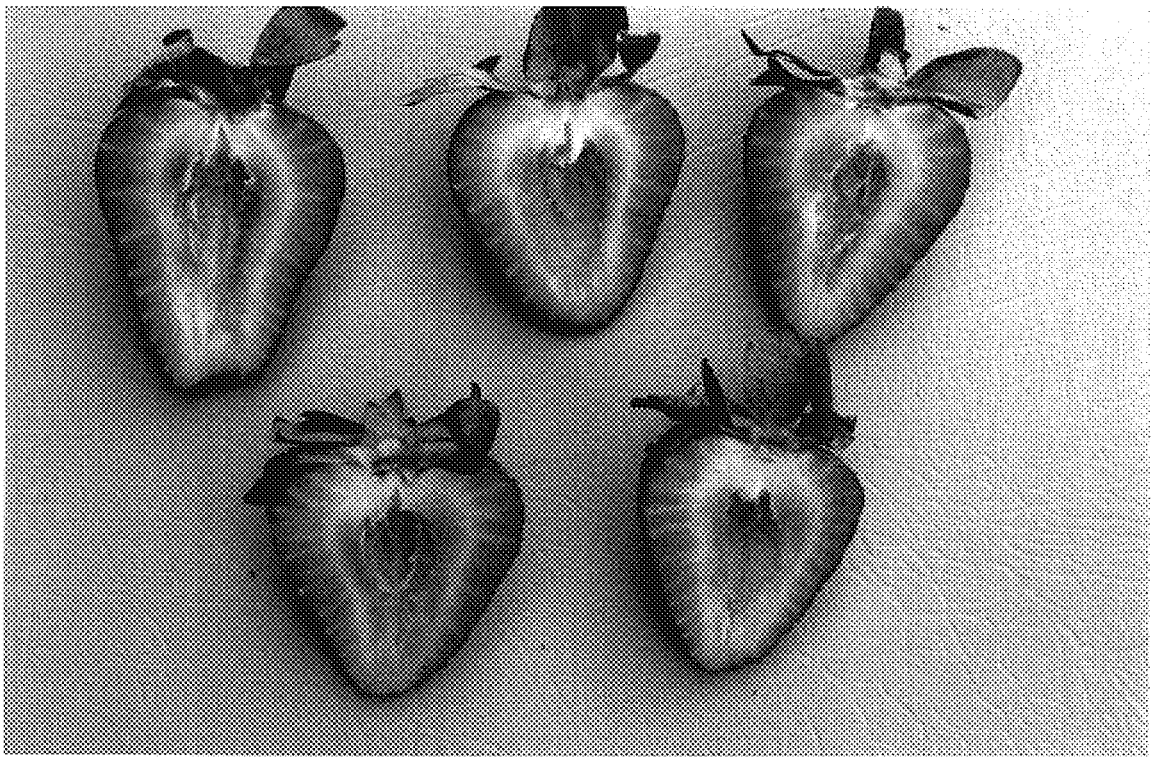
FIG. 5 shows the fruit in longitudinal cross-section.

The following description of 'DrisStrawFour' is based on observations taken from the 2000 to 2005 growing seasons in Hillsborough County, Florida. This description is in accordance with UPOV terminology. Color designations, color descriptions, and other phenotypical descriptions may deviate from the stated values and descriptions depending upon variation in environmental, seasonal, climatic and cultural conditions. 'DrisStrawFour' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of the male parent 'Driscoll Mirador' (U.S. Plant Pat. No. 11,279). Plant characteristics include plant height, terminal leaf length, petiole length, fruit length, fruit width and *Botrytis* fruit rot.

TABLE 1

| Characteristic | 'DrisStrawFour' | 'Driscoll Mirador' |
|---|---|---|
| Plant height (cm) | 20.9 | 13.5 |
| Terminal leaf length (cm) | 8.3 | 7.7 |
| Petiole length (cm) | 11.2 | 9.2 |
| Fruit length (cm) | 4.5 | 3.4 |
| Fruit width (cm) | 4.2 | 2.4 |
| *Botrytis* fruit rot | Moderately resistant | Moderately susceptible |

Table 2 shows plant characteristics of the new variety compared with plant characteristics of the commercial varieties, 'Driscoll Malibu' (U.S. Plant Pat. No. 16,070) and 'Driscoll Osceola' (U.S. Plant Pat. No. 15,752). Plant characteristics include plant height, diameter, number of crowns per plant, habit, density of individual plant and vigor.

TABLE 2

| Characteristic | 'DrisStrawFour' | 'Driscoll Malibu' | 'Driscoll Osceola' |
|---|---|---|---|
| Plant height (cm) | 20.9 | 17.9 | 18.5 |
| Plant diameter (cm) | 40.7 | 39.8 | 38.2 |

TABLE 2-continued

| Characteristic | 'DrisStrawFour' | 'Driscoll Malibu' | 'Driscoll Osceola' |
|---|---|---|---|
| Number of crowns/plant | 4 | 4 | 2 |
| Habit | Between flat globose and flat | Globose | Flat globose |
| Density of individual plant | Between medium and dense | Medium | Between open and medium |
| Vigor | Strong | Between weak and medium | Medium |

Table 3 shows leaf characteristics of the new cultivar compared with leaf characteristics of 'Driscoll Malibu' and 'Driscoll Osceola'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, leaflet margin, and shape of leaf base.

TABLE 3

| Leaf Characteristic | 'DrisStrawFour' | 'Driscoll Malibu' | 'Driscoll Osceola' |
|---|---|---|---|
| Terminal leaflet length (cm) | 8.3 | 9.3 | 10.3 |
| Terminal leaflet width (cm) | 8.2 | 9.3 | 10.4 |
| Terminal leaflet length/width ratio | 1.02 | 1.00 | 0.98 |
| No. teeth/terminal leaflet | 25 | 23 | 11 |
| Shape of teeth | Rounded | Between obtuse and rounded | Obtuse |
| Color of upperside of leaf | RHS 137A Dark green | RHS 141A Dark bright green | RHS 135B Dark bright blue-green |
| Color of underside of leaf | RHS 148C Medium yellow-green | RHS 139C Medium green | RHS 138B Medium green |
| Leaf shape in cross section | Concave | Between slightly concave and flat | Between concave and slightly concave |
| Leaf blistering | Strong | Medium | Medium |
| Leaf glossiness | Medium | Weak | Medium |
| No. leaflets | Three only | Three only | Three only |
| Terminal leaflet margin | Flat | Flat | Flat |
| Terminal leaflet: length/width ratio | As long as broad | As long as broad | As long as broad |
| Terminal leaflet base shape | Obtuse | Rounded | Rounded |

Table 4 shows information about the petiole, the petiolule, the bract, and the stipule of the new cultivar compared to 'Driscoll Malibu' and 'Driscoll Osceola'. This includes petiole length in centimeters, petiole diameter in centimeters, petiolule length in centimeters, petiolule diameter in centimeters, bract frequency per petiole, stipule length in centimeters, stipule width in centimeters, stipule pubescence, petiole pubescence, pose of hairs on the petiole, color of the petiole and color of the petiolule.

TABLE 4

| Characteristic | 'DrisStrawFour' | 'Driscoll Malibu' | 'Driscoll Osceola' |
|---|---|---|---|
| Petiole length (cm) | 11.2 | 10.5 | 9.1 |
| Petiole diameter (cm) | 0.417 | 0.402 | 0.406 |
| Petiole pubescence | Between sparse and medium | Dense | Dense |
| Petiole pose of hairs | Upwards | Downwards | Between outwards and downwards |
| Petiole color | RHS 145A Light yellow-green | RHS 144B Bright yellow-green | RHS 141C Bright medium green |
| Petiolule color | RHS 145C Light yellow-green | | |
| Petiolule length (cm) | 1.096 | 1.424 | 1.205 |
| Petiolule diameter (cm) | 0.232 | 0.260 | 0.251 |
| Bract frequency | 1 | 1 | 0 |
| Stipule length (cm) | 3.8 | 4.0 | 4.5 |
| Stipule width (cm) | 1.047 | 1.162 | 1.091 |
| Stipule pubescence | Medium | Medium | Medium |

Table 5 shows stolon characteristics of the new cultivar compared to 'Driscoll Malibu' and 'Driscoll Osceola'. These characteristics include the number of stolons, the anthocyanin coloration of the stolons, the thickness of the stolons, and the pubescence of the stolons.

TABLE 5

| Characteristic | 'DrisStrawFour' | 'Driscoll Malibu' | 'Driscoll Osceola' |
|---|---|---|---|
| Stolon Number | Few | Few | Few |
| Stolon Anthocyanin | Very strong | Between medium and strong | Between medium and strong |
| Stolon Thickness | Thick | Between medium and thick | Between medium and thick |
| Stolon Pubescence | Sparse | Medium | Dense |

Table 6 shows inflorescence characteristics of the new cultivar compared to 'Driscoll Malibu' and 'Driscoll Osceola'. These characteristics include inflorescence position relative to foliage, relative flower size, flower diameter in centimeters (measured from petal tip to petal tip), relative spacing of petals, petal length in centimeters, petal width in centimeters, petal length to width ratio, petal color, calyx diameter in centimeters (measured on back of flower from sepal tip to sepal tip), diameter of calyx relative to corolla, diameter of inner calyx relative to outer, sepal length in centimeters (measured from sepal tip to point of attachment to receptacle), sepal width in centimeters, receptacle color and anther color.

TABLE 6

| Characteristic | 'DrisStrawFour' | 'Driscoll Malibu' | 'Driscoll Osceola' |
|---|---|---|---|
| Inflorescence position relative to foliage | Between level with and above | Between level with and above | Between level with and above |

TABLE 6-continued

| Characteristic | 'DrisStrawFour' | 'Driscoll Malibu' | 'Driscoll Osceola' |
|---|---|---|---|
| Flower size | Medium | Medium | Medium |
| Flower diameter (cm) | 3.014 | 2.525 | 3.045 |
| Petal spacing | Overlapping | Overlapping | Overlapping |
| Petal length (cm) | 1.278 | 1.290 | 1.623 |
| Petal width (cm) | 1.463 | 1.429 | 1.698 |
| Petal length/width ratio | 0.87 | 0.90 | 0.96 |
| Petal length/width ratio | Broader than long | Between much broader than long and broader than long | Between as long as broad and longer than broad |
| Petal color | RHS 155C White | RHS 155C White | RHS 155C White |
| Calyx diameter (cm) | 3.776 | 4.021 | 5.659 |
| Calyx diameter relative to corolla | Larger | Larger | Larger |
| Inner calyx diameter relative to outer | Same size | Larger | Between smaller and same size |
| Sepal length (cm) | 1.252 | 1.396 | 2.147 |
| Sepal width (cm) | 0.718 | 0.796 | 1.182 |
| Receptacle color | RHS 9A Bright golden yellow | | |
| Anther color | RHS 12A Golden yellow | | |

Table 7 shows fruit characteristics of the new cultivar compared to 'Driscoll Malibu' and 'Driscoll Osceola'.

TABLE 7

| Characteristic | 'DrisStrawFour' | 'Driscoll Malibu' | 'Driscoll Osceola' |
|---|---|---|---|
| Fruiting truss length (cm) | 19.1 | 17.4 | 19.9 |
| Fruiting truss attitude | Prostrate | Prostrate | Prostrate |
| Fruiting truss length | Between short and medium | Short | Between short and medium |
| Fruit length (cm) | 4.517 | 4.921 | 4.223 |
| Fruit width (cm) | 4.183 | 3.960 | 3.968 |
| Fruit length/width ratio | 1.08 | 1.24 | 1.06 |
| Fruit length/width ratio | As long as broad | Between as long as broad and longer than broad | As long as broad |
| Fruit weight (g) | 28 | 28 | 30 |
| Relative fruit size | Medium | Between medium and large | Between small and medium |
| Predominant fruit shape | Cordate | Conical | Cordate |
| Difference in shape between primary & secondary fruits | Slight | Slight | Slight |
| Band without achenes | Medium | Between absent and very narrow | Between absent and very narrow to narrow |
| Unevenness of fruit surface | Between absent and very weak | Medium | Weak |
| Fruit skin color | RHS 46A Dark red | RHS 46B Dark bright red | RHS 46A Dark red |
| Evenness of fruit color | Even | Slightly uneven | Slightly uneven |
| Fruit glossiness | Between medium and strong | Strong | Strong |

TABLE 7-continued

| Characteristic | 'DrisStrawFour' | 'Driscoll Malibu' | 'Driscoll Osceola' |
|---|---|---|---|
| Insertion of achenes | Level with surface | Between below surface and level with surface | Below surface |
| Achene coloration-sunward side of berry | RHS 181A Dark greyed-red | | |
| Achene coloration-shaded side of berry | RHS 13A Golden yellow | | |
| Achenes per berry | 356 | | |
| Achene weight | 0.0014 | | |
| Insertion of calyx | Level | Level | Level |
| Pose of calyx segments | Between spreading and reflexed | Reflexed | Between spreading and reflexed |
| Size of calyx in relation to fruit | Between same size and larger | Between same size and larger | Between same size and larger |
| Adherence of calyx | Strong | Strong | Strong |
| Firmness of flesh | Medium | Between soft and medium | Between soft and medium |
| Color of the flesh | RHS 44B Bright red and RHS 155C White | RHS 48C Medium pink | RHS 48D Light pink |
| Evenness of flesh color | Slightly uneven | Slightly uneven | Slightly uneven |
| Distribution of flesh color | Marginal and central | Marginal and central | Marginal and central |
| Hollow center | Large | Small | Medium |
| Sweetness | Strong | Medium | Medium |
| Acidity | Medium | Medium | Medium |
| Texture when tasted | Medium | Medium | Fine |
| Time of flowering | Very early | Very early | Very early |
| Harvest maturity (50% of plants with ripe fruit) | Early-Mid November to early April | Late | Late |
| Type of bearing | Fully everbearing | Partially everbearing | Partially everbearing |
| Grams of fruit/plant | 443 | 287 | 422 |

Table 8 shows the resistance to different forms of stress of the new cultivar compared to 'Driscoll Malibu' and 'Driscoll Osceola'. These forms of stress include high temperatures and pesticides.

TABLE 8

| Reaction to Stress | 'DrisStrawFour' | 'Driscoll Malibu' | 'Driscoll Osceola' |
|---|---|---|---|
| High temperatures | Moderately resistant | | |

Table 9 shows pest and disease characteristics of the new cultivar compared to 'Driscoll Malibu' and 'Driscoll Osceola'.

TABLE 9

| Pest or Disease | 'DrisStrawFour' | 'Driscoll Malibu' | 'Driscoll Osceola' |
|---|---|---|---|
| *Tetranychus urticae* (2-spotted spider mite) | Moderately susceptible | Susceptible | Susceptible |
| *Tarsonemus pallidus* | Moderately resistant | | |

TABLE 9-continued

| Pest or Disease | 'DrisStrawFour' | 'Driscoll Malibu' | 'Driscoll Osceola' |
|---|---|---|---|
| *Aphelencoides fragariae* | Moderately resistant | | |
| *Pratylenchus penetrans* | Moderately susceptible | | |
| *Aphis* spp. (Aphids) | Moderately susceptible | | |
| *Lygus hesperus* (Lygus bug) | Moderately resistant | Susceptible | Susceptible |
| *Botrytis* fruit rot | Moderately resistant | Susceptible | Susceptible |
| Powdery mildew | Moderately resistant | Moderately susceptible | Moderately susceptible |
| *Verticillium* wilt | Resistant | Highly susceptible | Susceptible |
| Leather rot | Resistant | | |
| Red stele *Phytophthora fragariae* | Moderately resistant | | |

TABLE 9-continued

| Pest or Disease | 'DrisStrawFour' | 'Driscoll Malibu' | 'Driscoll Osceola' |
|---|---|---|---|
| *Ramularia tulasnei*-Leaf spots | Moderately resistant | | |
| Leaf scorch | Resistant | | |
| Leaf blight | Resistant | | |
| Black root rot | Resistant | | |
| Viral diseases-Strawberry Mottle Virus | Moderately resistant | Susceptible | Susceptible |
| *Xanthomonas fragariae* | Moderately susceptible | Moderately susceptible | Moderately susceptible |

We claim:

1. A new and distinct cultivar of strawberry plant as described and shown herein.

* * * * *